US005788955A

United States Patent [19]
Eteve et al.

[11] Patent Number: 5,788,955
[45] Date of Patent: Aug. 4, 1998

[54] SCREENING COSMETIC COMPOSITION CONTAINING A MIXTURE OF 1,4-BENZENEDI (3-METHYLIDENE-10-CAMPHOSULFONIC) ACID, PARTIALLY OR COMPLETELY NEUTRALIZED, AND METAL OXIDE NANOPIGMENTS

[75] Inventors: Martine Eteve; Isabelle Hansenne, both of Paris, France

[73] Assignee: L'Oreal, Paris, France

[21] Appl. No.: 458,192

[22] Filed: Jun. 2, 1995

Related U.S. Application Data

[62] Division of Ser. No. 119,651, Sep. 13, 1993, Pat. No. 5,643,557, which is a continuation of Ser. No. 897,498, Jun. 12, 1992, abandoned.

[30] Foreign Application Priority Data

Jun. 13, 1991 [FR] France .................... 91 07255

[51] Int. Cl.$^6$ ................ A61K 7/42; A61K 7/00
[52] U.S. Cl. ................ 424/60; 424/59; 424/63; 424/70.9; 514/972
[58] Field of Search ............... 424/401, 63, 59, 424/70.9, 60; 514/972

[56] References Cited

U.S. PATENT DOCUMENTS

| | | | |
|---|---|---|---|
| 4,710,373 | 12/1987 | Nakamura et al. | 424/59 |
| 5,028,417 | 7/1991 | Bhat | 424/59 |
| 5,032,390 | 7/1991 | Iwaya | 424/59 |
| 5,044,594 | 9/1991 | Richard | 424/97 |
| 5,093,099 | 3/1992 | Haishi | 423/622 |

FOREIGN PATENT DOCUMENTS

| | | |
|---|---|---|
| 0303995 | 2/1989 | European Pat. Off. . |
| 0370867 | 5/1990 | European Pat. Off. . |
| 3824999 | 2/1989 | Germany . |
| 9011067 | 10/1990 | WIPO . |

OTHER PUBLICATIONS

French Search Report—FR 9107255.

*Primary Examiner*—Sally Gardner-Lane
*Attorney, Agent, or Firm*—Nixon & Vanderhye, P.C.

[57] ABSTRACT

The invention relates to a screening cosmetic composition comprising, in a mixture, 0.5 to 10% by weight of metal oxide nanopigments chosen from titanium, zinc, cerium or zirconium oxide or mixtures thereof, with a mean diameter of less than 100 nm, and 0.1 to 10% by weight of 1,4-benzenedi(3-methylidene-10-camphosulfonic) acid or one of its alkali metal, ammonium, amine, alkanolamine, Ca, Zn, Mg, Ba, Al or Zr salts, in a cosmetically acceptable carrier.

This composition is useful as composition for protecting the human epidermis or the hair against UV rays or as make-up.

14 Claims, No Drawings

SCREENING COSMETIC COMPOSITION CONTAINING A MIXTURE OF 1,4-BENZENEDI (3-METHYLIDENE-10-CAMPHOSULFONIC) ACID, PARTIALLY OR COMPLETELY NEUTRALIZED, AND METAL OXIDE NANOPIGMENTS

This is a division of application Ser. No. 08/119,561, now U.S. Pat. No. 5,643,557, filed Sep. 13, 1995, which is a continuation of application Ser. No. 07/897,498 filed Jun. 12, 1992, now abandoned.

The subject of the present invention is a screening cosmetic composition containing 1,4-benzenedi(3-methylidene-10-camphosulfonic) acid, partially or completely neutralized, and at least one metal oxide nanopigment, as well as its use for protecting the human epidermis and the hair and as make-up.

1,4-Benzenedi(3-methylidene-10-camphosulfonic) acid and its salts, which are described in French Patents no. 2,528,420 and 2,639,347, by the applicant, are so-called broad-band screening agents which absorb ultraviolet rays with wavelengths of between 280 and 400 nm, and with absorption maxima of between 320 and 400 nm, being situated in particular at around 345 nm. However, cosmetic compositions containing such screening agents have the disadvantage of leaving a relatively sticky feel on the skin and the hair.

Moreover, the efficacy of cosmetic compositions containing these broad-spectrum UV screening agents, expressed as the light-protection factor which is called "protection index or PI", is good but still proves to be inadequate for very sensitive skins or skins continually exposed to solar radiation.

The protection index or PI may be expressed by the ratio of the irradiation time required to reach the erythematogenic threshold with the UV screening agent to the irradiation time required to reach the erythematogenic threshold without the UV-screening agent.

Furthermore, the use of conventional metal oxides with a particle size of between 100 and 700 nm, such as titanium oxide, in make-up where the said titanium oxide is used as opacifying white pigment in combination with colored pigments, is known. These compounds are particularly advantageous because of their ultraviolet radiation-diffusion and reflection properties which enable the human epidermis to be protected against ultraviolet rays. However, when the concentration of titanium oxide in a cosmetic composition is increased in order to enhance the protection against ultraviolet rays, a cosmetic product is obtained which is difficult to apply to the skin, which is opaque and which leaves a whitish film on the skin, after application, which is disliked by users.

Attempts were therefore made to reduce the particle size of the metal oxide pigments. However, it was discovered that the exposure of metal oxide pigments with a particle size of less than 100 nm, called "nanopigments", to light may generate a light-induced reaction which is prejudicial to the stability of the cosmetic compositions, in particular those containing lipids.

According to the invention, it has been discovered, surprisingly, that the combination of metal oxide nanopigments, with a particle size of less than 100 nm, with partially or completely neutralized 1,4-benzenedi(3-methylidene-10-camphosulfonic) acid, in a cosmetic composition, makes it possible on the one hand, to improve the cosmetic properties of the said composition and especially to reduce the sticking effect of the screening agent and the residual whitening of the skin after application, and on the other hand, to reduce or inhibit the light-induced reaction of metal oxide nanopigments. The cosmetic compositions thus obtained also possess a high protection index in UV-B and, by virtue of their high absorption in UV-A, they make it possible to prevent the development of photodermatoses, including benign or polymorphous summer light-induced cutaneous lesions. Furthermore, they are highly resistant to water, that is to say that the protection index is highly stable over time, especially after a shower or a swim.

The subject of the present invention is therefore a screening cosmetic composition containing, in a mixture, partially or completely neutralized 1,4-benzene-di (3-methylidene-10-camphosulfonic) acid of formula (I) below, and at least one metal oxide nanopigment in a cosmetically acceptable carrier.

Partially or completely neutralized 1,4-benzene-di (3-methylidene-10-camphosulfonic) acid is of formula:

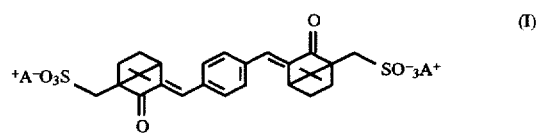

in which A denotes a hydrogen atom, an alkali metal, an $NH(R)_3^+$ group, the R radicals being identical or different and denoting a hydrogen atom or a $C_1$–$C_4$ alkyl or hydroxyalkyl radical, or alternatively an $M^{n+}/n$ group where $M^{n+}$ is a polyvalent metal cation in which n is equal to 2 or 3 or 4, $M^{n+}$ preferably denoting $Ca^{2+}$, $Zn^{2+}$, $Mg^{2+}$, $Ba^{2+}$, $Al^{3+}$ or $Zr^{4+}$.

It is of course understood that the compound of formula (I) can give rise to the "cis-trans" isomer around one or more double bond(s) and that all the isomers form part of the invention.

In the present application, "nanopigment" will be understood to mean a pigment with a mean diameter of less than 100 nm, and preferably of between and 5 and 50 nm.

The metal oxides are chosen from titanium, zinc, cerium or zirconium oxides or mixtures thereof.

The nanopigments may be coated or uncoated.

The coated pigments are pigments which have undergone one or more surface treatments of a chemical, electronic, mechanicochemical and/or mechanical nature, with compounds as described for example in Cosmetics & Toiletries, February 1990, Vol. 105, p. 53–64, such as amino acids, beeswax, fatty acids, fatty alcohols, anionic surface-active agents, lecithins, sodium, potassium, zinc, iron or aluminum salts of fatty acids, (titanium or aluminum) metal alkoxides, polyethylene, silicones, proteins (collagen, elastin), alkanolamines, silicon oxides, metal oxides or sodium hexametaphosphate.

The coated pigments are more particularly titanium oxides coated with:

silica such as the product "SUNVEIL" from the company IKEDA, silica and iron oxide such as the product "SUNVEIL F" from the company IKEDA, silica and alumina such as the products "MICROTITA-NIUM DIOXIDE MT 500 SA" and "MICROTITA-NIUM DIOXIDE MT 100 SA" from the company TAYCA, "TIOVEIL" from, the company TIOXIDE, alumina such as the products "TIPAQUE TTO-55 (B)" and "TIPAQUE TTO-55 (A)" from the company ISHIHARA, and "UVT 14/4" from the company KEMIRA, alumina and aluminum stearate such as the product "MICROTITANIUM DIOXIDE MT 100 T" from the company TAYCA.

alumina and aluminum laurate such as the product "MICROTITANIUM DIOXIDE MT 100 S" from the company TAYCA.

iron oxide and iron stearate such as the product "MICROTITANIUM DIOXIDE MT 100 F" from the company TAYCA.

zinc oxide and zinc stearate such as the product "BR 351" from the company TAYCA.

silica, alumina and silicone such as the products "MICROTITANIUM DIOXIDE MT 600 SAS" and "MICROTITANIUM DIOXIDE MT 500 SAS" from the company TAYCA.

silica, alumina, aluminum stearate and silicone such as the product "STT-30-DS" from the company TITAN KOGYO.

alumina and silicone such as the product "TIPAQUE TTO 55 (S)" from the company ISHIHARA.

triethanolamine such as the product "STT-65-S" from the company TITAN KOGYO.

stearic acid such as the product "TIPAQUE TTO-55(C)" from the company ISHIHARA.

sodium hexametaphosphate such as the product "MICROTITANIUM DIOXIDE MT 150 W" from the company TAYCA.

Mixtures of metal oxides may also be mentioned, especially of titanium dioxide and cerium dioxide including the silica-coated equiponderous mixture of titanium dioxide and cerium dioxide sold by the company IKEDA under the name "SUNVEIL A", as well as the alumina, silica and silicone-coated mixture of titanium dioxide and zinc dioxide such as the product "H 261" sold by the company KEMIRA, or the alumina, silica and glycerin-coated mixture of titanium dioxide and zinc dioxide such as the product "M 211" sold by the company KEMIRA.

The uncoated titanium oxides are for example sold by the company TAYCA under the trade names "MICROTITANIUM DIOXIDE MT 500 B" or "MICROTITANIUM DIOXIDE MT 600 B", by the company DEGUSSA under the name "P 25", by the company WACKHERR under the name "Oxyde de titane transparent PW", by the company MIYOSHI KASEI under the name "UFTR", by the company TOMEN under the name "ITS" and by the company TIOXIDE under the name "TIOVEIL AQ".

The uncoated zinc oxides are for example sold by the company SUMITOMO under the name "ULTRA FINE ZINC OXIDE POWDER" by the company PRESPERSE under the name "FINEX 25" or by the company IKEDA under the name "MZO-25".

The uncoated cerium oxide is sold under the name "COLLOIDAL CERIUM OXIDE" by the company RHONE POULENC.

According to the invention, the coated or uncoated titanium oxide nanopigments are particularly preferred.

The partially or completely neutralized 1,4-benzenedi(3-methylidene-10-camphosulfonic) acid of formula (I) above is advantageously present it the cosmetic composition according to the invention at a concentration, calculated on the basis of the acid, of between 0.1 and 10% by weight, preferably between 0.25 and 5% by weight relative to the total weight of the composition.

The metal oxide nanopigments are advantageously present in the cosmetic composition according to the invention at a concentration of between 0.5 and 10% by weight, preferably of between 1 and 7% by weight relative to the total weight of the composition.

The 1,4-benzenedi(3-methylidene-10-camphosulfonic) acid/metal oxide nanopigment weight ratio is advantageously between 0.05 and 5, preferably between 0.07 and 3.

The cosmetic composition of the invention may be used as a composition for protecting the human epidermis or the hair against ultraviolet rays, as anti-sun composition or as make-up.

This composition may be provided in particular in the form of a lotion, thickened lotion, gel, vesicular dispersion, cream, milk, powder, solid stick and it may be optionally packaged as an aerosol and provided in the form of a foam or spray.

It may contain the cosmetic adjuvants normally used, such as fatty substances, organic solvents, silicones, thickeners, demulcents, UV-A, UV-B or broad-band sunscreen agents, antifoaming agents, moisturizing agents, perfumes, preservatives, surface-active agents, fillers, sequestrants, anionic, cationic, nonionic or amphoteric polymers or mixtures thereof, propellants, alkalizing or acidifying agents, colorants, metal oxide pigments with a particle size of between 100 nm and 20,000 nm such as iron oxides, or any other ingredient normally used in cosmetics.

Among the organic solvents, lower alcohols and polyols such as ethanol, isopropanol, propylene glycol, glycerin and sorbitol may be mentioned.

The fatty substances may consist of an oil or a wax or a mixture thereof, of fatty acids, fatty acid esters, fatty alcohols, vaseline, paraffin, lanolin, hydrogenated lanolin or acetylated lanolin.

The oils are chosen from animal, vegetable, mineral or synthetic oils and especially hydrogenated palm oil, hydrogenated castor oil, vaseline oil, paraffin oil, Purcellin oil, silicone oils and isoparaffins.

The waxes are chosen from-animal, fossil, vegetable, mineral or synthetic waxes. Beeswaxes, Carnauba, Candelilla, sugar cane or Japan waxes, ozokerites, Montan wax, microcrystalline waxes, paraffins or silicone waxes and resins may be particularly mentioned.

The fatty acid esters are for example isopropyl myristate, isopropyl adipate, isopropyl palmitate, octyl palmitate, $C_{12}$–$C_{15}$ fatty alcohol benzoates ("FINSOLV TN" from FINETEX), oxypropylenated myristic alcohol containing 3 moles of propylene oxide ("WITCONOL APH" from WITCO), capric and caprylic acid triglycerides ("MIGLYOL 812" from HULS).

The cosmetic composition according to the invention may also contain thickeners which may be chosen from cross-linked or non cross-linked acrylic acid polymers, and particularly polyacrylic acids which are cross-linked using a polyfunctional agent, such as the products sold under the name "CARBOPOL" by the company GOODRICH, cellulose derivatives such as methylcellulose, hydroxyethyl cellulose, hydroxypropyl methylcellulose, sodium salts of carboxymethylcellulose, or mixtures of cetylstearyl alcohol and oxyethylenated cetylstearyl alcohol containing 33 moles of ethylene oxide.

The products derived from the ionic interaction of a cationic polymer consisting of a copolymer of cellulose or a cellulose derivative grafted via a water-soluble quaternary ammonium monomer salt, and an anionic carboxylic polymer, such as described in French Patent FR-2,598,611, may also be used. The product of the ionic interaction of a hydroxyethyl cellulose copolymer grafted via a radical-based method, via diallyldimethylammonium chloride, such as the polymer marketed under the name "CELQUAT L 200" by the company NATIONAL STARCH, with either ethylene and maleic anhydride copolymers such as the products sold under the name "EMA 31" by the company MONSANTO, or with 50/50 methacrylic acid and methyl methacrylate copolymers, are preferably used.

Another product of this type which may be used is the product derived from the ionic interaction of hydroxyethyl cellulose copolymer grafted via a radical-based method, via diallyldimethylammonium chloride, with a cross-linked carboxylic anionic polymer such as the cross-linked methacrylic acid and ethyl acrylate copolymers sold under the name "VISCOATEX" 538, 46 or 50 by the company COATEX.

When the cosmetic composition according to the invention is used for protecting the human epidermis against UV rays, as anti-sun composition or as composition enabling photodermatoses and burns to be prevented, it may be provided in the form of a suspension or dispersion in solvents or fatty substances, or alternatively in the form of an emulsion such as a cream or milk, in the form of an ointment, gel, solid stick or aerosol foam. The emulsions may contain, in addition, anionic, nonionic, cationic or amphoteric surface-active agents.

It may also be provided in the form of a vesicular dispersion of ionic or nonionic amphiphilic lipids, which is prepared according to known processes. For example, the lipids may be swollen in an aqueous solution so as to form dispersed spherules in the aqueous medium as described in the article BANGHAN, STANDISH & WATKINS, J. Mol. Biol., 13, 238 (1965) or in patents FR-2,315,991 and 2,416, 008 by the applicant.

When the cosmetic composition according to the invention is used for protecting the hair, it may be provided in the form of a rinse-off shampoo, lotion, gel or composition to be applied before or after shampooing, before or after dyeing or bleaching, before, during or after permanent waving or hair straightening, a hair styling or treatment lotion or gel, a lotion or gel for blow-drying or hair setting, hair lacquer, or composition for permanent waving or hair straightening, for dyeing or bleaching the hair.

When the composition is used as make-up for the eyelashes, eyebrows, the skin or the hair, such as cream for treating the epidermis, foundation, lipstick, eyeshadow, blusher, eyeliner, mascara or coloring gel, it may be provided in anhydrous or aqueous solid or pasty form, as oil-in-water or water-in-oil emulsions, as suspensions or alternatively as gels.

The subject of the invention is also a process for protecting the human epidermis and the hair against ultraviolet radiation as well as a process for applying make-up, which consist in applying to the skin or the hair an effective amount of the above cosmetic composition.

The subject of the invention is also the use of the above defined composition in the preventive treatment of photodermatoses including benign or polymorphous summer light-induced cutaneous lesions.

Another subject of the invention relates to the use of partially or completely neutralized 1,4-benzenedi-(3-methylidene-10-camphosulfonic) acid for reducing or inhibiting the light-induced reaction of metal oxide nanopigments exposed to light, these metal oxides being chosen from titanium, zinc, cerium or zirconium oxides or mixtures thereof with a mean diameter of less than 100 nm, and preferably of between 5 and 50 nm.

The invention will be better illustrated by the non-limitative examples below.

EXAMPLE 1

An oil-in-water anti-sun emulsion of the following composition is prepared:

| | |
|---|---|
| 1,4-Benzenedi(3-methylidene-10-camphosulfonic) acid | 5.0 g |
| Alumina and aluminum stearate-coated titanium oxide sold under the name "MICROTITANIUM DIOXIDE MT 100T" by the company TAYCA | 5.0 g |
| Mixture of cetylstearyl alcohol and oxyethylenated cetylstearyl alcohol containing 33 moles of ethylene oxide sold under the name "SINNOWAX AO" by the company HENKEL | 7.0 g |
| Non-self-emulsifying glycerol mono- and distearate mixture | 2.0 g |
| $C_{12}$–$C_{15}$ alcohol benzoate sold under the name "FINSOLV TN" by the company FINETEX | 15.0 g |
| Cetyl alcohol | 1.5 g |
| Polydimethylsiloxane | 1.5 g |
| Glycerin | 20.0 g |
| Triethanolamine qs pH 7 | |
| Preservatives, perfume qs | |
| Water qs | 100 g |

EXAMPLE 2

An oil-in-water anti-sun emulsion of the following composition is prepared:

| | |
|---|---|
| 1,4-Benzenedi(3-methylidene-10-camphosulfonic) acid | 1.0 g |
| Alumina and aluminum stearate-coated titanium oxide sold under the name "MICROTITANIUM DIOXIDE MT 100T" by the company TAYCA | 6.0 g |
| 3-(4-Methylbenzylidene)camphor sold under the name "EUSOLEX 6300" by the company MERCK | 3.0 g |
| 4-tert-Butyl-4'-methoxydibenzoylmethane sold under the name "PARSOL 1789" by the company GIVAUDAN | 1.0 g |
| Mixture of cetylstearyl alcohol and oxyethylenated cetylstearyl alcohol containing 33 moles of ethylene oxide sold under the name "SINNOWAX AO" by the company HENKEL | 7.0 g |
| Non-self-emulsifying glycerol mono- and distearate mixture | 2.0 g |
| $C_{12}$–$C_{15}$ alcohol benzoate sold under the name "FINSOLV TN" by the company FINETEX | 15.0 g |
| Cetyl alcohol | 1.5 g |
| Polydimethylsiloxane | 1.5 g |
| Glycerin | 20.0 g |
| Triethanolamine qs pH 7 | |
| Preservative, perfume qs | |
| Water qs | 100 g |

This composition may be applied so as to prevent benign or polymorphous light-induced cutaneous lesions.

EXAMPLE 3

An oil-in-water anti-sun emulsion of the following composition is prepared:

| | |
|---|---|
| 1,4-Benzenedi(3-methylidene10-camphosulfonic) acid | 2.0 g |
| Alumina and aluminum stearate-coated titanium oxide sold under the name "MICROTITANIUM DIOXIDE MT 100T" by the company TAYCA | 4.0 g |
| 2-Ethylhexyl α-cyano-β,β-diphenylacrylate | 6.0 g |

-continued

| | |
|---|---|
| sold under the name "UVINUL N 539" by the company BASF | |
| 4-tert-Butyl-4'-methoxydibenzoylmethane sold under the name "PARSOL 1789" by the company GIVAUDAN | 2.0 g |
| Mixture of cetylstearyl alcohol and oxyethylenated cetylstearyl alcohol containing 33 moles of ethylene oxide sold under the name "SINNOWAX AO" by the company HENKEL | 7.0 g |
| Non self-emulsifying glycerol mono- and distearate mixture | 2.0 g |
| $C_{12}$–$C_{15}$ alcohol benzoate sold under the name "FINSOLV TN" by the company FINETEX | 15.0 g |
| Cetyl alcohol | 1.5 g |
| Polydimethylsiloxane | 1.5 g |
| Glycerin | 20.0 g |
| Triethanolamine qs pH 7 | |
| Preservatives, perfume qs | |
| Water qs | 100 g |

EXAMPLE 4

An oil-in-water anti-sun emulsion of the following composition is prepared:

| | |
|---|---|
| 1,4-Benzenedi(3-methylidene-10-camphosulfonic) acid | 5.0 g |
| Zinc oxide sold under the name "ULTRA FINE ZINC POWDER" by the company SUMITOMO | 5.0 g |
| Mixture of cetylstearyl alcohol and oxyethylenated cetylstearyl alcohol containing 33 moles of ethylene oxide sold under the name "SINNOWAX AO" by the company HENKEL | 7.0 g |
| Non-self-emulsifying glycerol mono- and distearate mixture | 2.0 g |
| $C_{12}$–$C_{15}$ alcohol benzoate sold under the name "FINSOLV TN" by the company FINETEX | 15.0 g |
| Cetyl alcohol | 1.5 g |
| Polydimethylsiloxane | 1.5 g |
| Glycerin | 20.0 g |
| Triethanolamine qs pH 7 | |
| Preservatives, perfume qs | |
| Water qs | 100 g |

EXAMPLE 5

An oil-in-water anti-sun emulsion of the following composition is prepared:

| | |
|---|---|
| Aluminum salt of 1,4-benzenedi(3-methylidene-10-camphosulfonic) acid | 5.0 g |
| Alumina and aluminum stearate-coated titanium oxide sold under the name "MICROTITANIUM DIOXIDE MT 100T" by the company TAYCA | 5.0 g |
| Mixture of cetylstearyl alcohol and oxyethylenated cetylstearyl alcohol containing 33 moles of ethylene oxide sold under the name "SINNOWAX AO" by the company HENKEL | 7.0 g |
| Non-self-emulsifying glycerol mono- and distearate mixture | 2.0 g |
| $C_{12}$–$C_{15}$ alcohol benzoate sold under the name "FINSOLV TN" by the company FINETEX | 15.0 g |
| Cetyl alcohol | 1.5 g |
| Polydimethylsiloxane | 1.5 g |

-continued

| | |
|---|---|
| Glycerin | 20.0 g |
| Triethanolamine qs pH 7 | |
| Preservatives, perfume qs | |
| Water qs | 100 g |

EXAMPLE 6

A rinse-off conditioner of the following composition is prepared:

| | |
|---|---|
| 1,4-Benzenedi(3-methylidene-10-camphosulfonic) acid | 2.0 g |
| Cerium oxide (mean diameter 12 nanometers) in aqueous suspension containing 20% AI sold by the company RHONE POULENC under the name "COLLOIDAL CERIUM OXIDE" | 3.0 g AI |
| Polyoxyethylenated cetylstearyl alcohol containing 33 moles of ethylene oxide | 1.0 g |
| Cetylstearyl alcohol ($C_{16}$–$C_{18}$/50–50) | 2.0 g |
| Cetylstearyl alcohol ($C_{16}$–$C_{18}$/30–70) | 4.5 g |
| 2-Octyldodecanol | 0.8 g |
| Glycerin | 0.8 g |
| Stearyldimethylbenzylammonium chloride | 2.0 g |
| Protein hydrolysate (MW = 2500) carrying quaternary ammonium groups containing $C_{18}$ alkyl groups sold under the name "CROQUAT S" containing 43.7% AI by the company CRODA | 0.3 g AI |
| Triethanolamine qs pH 6.5 | |
| Preservative, perfume qs | |
| Water qs | 100 g |

EXAMPLE 7

A face-care cream of the following composition is prepared:

In a first stage, the following is melted while stirring gently at a temperature of 90° C.–95° C.; a mixture of 3.8 g of nonionic lipid of formula:

a formula wherein n has a mean statistical value equal to 3 and wherein —$C_3H_5$(OH)O— is represented by the following structures, taken together or separately:

$$-CH_2-CHO- \atop | \atop CH_2OH$$

$$-CH-CH_2O \atop | \atop CH_2OH$$

with 3.8 g of cholesterol and 0.4 g of monosodium glutamate salt of formula:

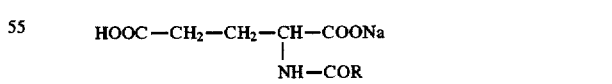

in which R is a mixture of hydrogenated $C_{14}$–$C_{22}$ alkenyl and/or alkyl radicals derived from tallow fatty acids, sold under the trade name "ACYLGLUTAMATE HS 11" by the company AJINOMOTO.

16 g of water, heated to 90° C., containing a preservative, are introduced into the melted mixture and mixed for about 6 to 8 minutes by means of an Ultra Turrax stirrer. 24 g of water are added, at room temperature, to the phase thus obtained and then the mixture is homogenized using an Ultra Turrax for a further 6 to 8 minutes before allowing the mixture to re-equilibrate to room temperature.

In a second stage, the following compounds are added:

| | |
|---|---|
| 1,4-Benzenedi(3-methylidene-10-campho-sulfonic) acid | 1.0 g |
| Cerium oxide (mean diameter 12 nanometers) in aqueous suspension containing 20% AI sold by the company RHONE POULENC under the name "COLLOIDAL CERIUM OXIDE" | 2.0 g AI |
| Glycerin | 3.0 g |
| Vaseline oil | 10.0 g |
| Preservative, perfume qs | |

A homogeneous aqueous gel consisting of 0.4 g of cross-linked polyacrylic acid sold under the name "CARBOPOL 940" by the company GOODRICH and 30 g of water containing a preservative are then added and the mixture is made up to 100 g with water.

The pH is adjusted to 6.5 with triethanolamine

EXAMPLE 8

A colored cream of the following composition is prepared:

| | |
|---|---|
| Non-self-emulsifying glycerol mono-and distearate mixture | 3.5 g |
| Glycerol isostearate | 1.8 g |
| Mixture of mineral oil and lanolin alcohol sold under the name "AMERCHOL L-101" by the company AMERCHOL | 3.1 g |
| Isopropyl palmitate | 7.6 g |
| Octyl palmitate | 7.0 g |
| Ultramarine violet | 0.75 g |
| Titanium dioxide with a particle size of 200–300 nm | 3.0 g |
| Yellow iron oxide | 1.0 g |
| Red iron oxide | 0.6 g |
| Black iron oxide | 0.08 g |
| Preservatives | 0.5 g |
| Perfume | 0.3 g |
| Aluminum and magnesium silicate | 1.5 g |
| Talc | 4.46 g |
| Triethanolamine | 1.2 g |
| Cellulose gum | 0.05 g |
| Xanthan gum | 0.15 g |
| Cyclomethicone ("CTFA Dictionary" name: cyclic dimethylpolysiloxane) | 7.5 g |
| Propylene glycol | 3.0 g |
| Glycerin | 2.0 g |
| Stearic acid | 2.5 g |
| Titanium dioxide with a particle size of 30–40 nm | 6.0 g |
| Zinc salt of 1,4-benzenedi(3-methylidene-10-camphosulfonic) acid | 2.0 g |
| Water qs | 100 g |

The fatty phase containing the oils and stearic acid and the aqueous phase containing triethanolamine are separately heated to 80° C.

The mixture is emulsified at 80° C. and cooled slowly. During the cooling, the mixture of pigments, previously ground in propylene glycol, and cyclomethicone are added.

EXAMPLE 9

A foundation of the following composition is prepared:

| | |
|---|---|
| Triethanolamine | 1.0 g |
| Polyethylene glycol stearate containing 2 moles of ethylene oxide | |
| Non-self-emulsifying glyercol mono- and distearate mixture | 0.35 g |
| Aluminum and magnesium silicate | 1.5 g |
| Yellow iron oxide | 0.9 g |
| Red iron oxide | 0.5 g |
| Black iron oxide | 0.2 g |
| Titanium dioxide with a particle size of 200–300 nm | 5.4 g |
| Titanium dioxide with a particle size of 30–40 nm | 8.0 g |
| Triethanolamine salt of 1,4-benzenedi-(3-methylidene-10-camphosulfonic) acid | 3.0 g |
| Preservatives | 0.5 g |
| Mixture of polyethylene glycol containing 6 moles of ethylene oxide and polyethylene glycol containing 32 moles of ethylene oxide sold under the name "CARBAWAX 1450" by the company UNION CARBIDE | 9.0 g |
| Cellulose gum | 0.02 g |
| Polyethylene | 9.3 g |
| Cyclomethicone (CTFA Dictionary name: cyclic dimethylpolysiloxane) | 14.0 g |
| Propylene glycol | 6.0 g |
| Glycerin | 3.0 g |
| Stearic acid | 2.2 g |
| Water qs | 100 g |

The composition is prepared in a manner similar to Example 8.

EXAMPLE 10

A foundation of the following composition is prepared:

| | |
|---|---|
| Non-self-emulsifying glycerol mono- and distearate mixture | 2.2 g |
| Caprylic-capric acid triglycerides | 15.0 g |
| Yellow iron oxide | 0.6 g |
| Yellow, brown iron oxides | 0.4 g |
| Black iron oxide | 0.2 g |
| Titanium dioxide with a particle size of 200–300 nm | 5.0 g |
| Methyl p-hydroxybenzoate | 0.1 g |
| Propyl p-hydroxybenzoate | 0.1 g |
| Preservatives | 0.3 g |
| 1,4-Benzenedi(3-methylidene10-campho-sulfonic) acid | 4.0 g |
| Magnesium and aluminum silicate | 1.0 g |
| Titanium oxide sold under the name "TIOVEIL AQ" by the company TIOXIDE | 10.0 g |
| Triethanolamine | 2.0 g |
| Sodium carboxymethylcellulose | 0.16 g |
| Aluminum salt of the reaction product of octenylsuccinic anhydride and starch sold under the name "DRYFLO" by the company NATIONAL STARCH | 5.0 g |
| Cyclopentadimethylsiloxane | 10.0 g |
| Propylene glycol | 2.0 g |
| Glycerin | 3.0 g |
| Sodium lauroylsarcosinate in solution in water at 30% AI sold under the name "ORAMIX L 30" by the company SEPPIC | 0.6 g |
| Stearic acid | 2.2 g |
| Water qs | 100 g |

We claim:

1. A sunscreening cosmetic composition comprising, in a cosmetically acceptable carrier, 0.5 to 10% by weight based on the total weight of said composition of a titanium oxide nanopigment with a mean diameter between 5 and 50 nm, mixed with 0.1 to 10% by weight of partially or completely neutralized 1,4-benzenedi(3-methylidene-10-camphosulfonic) acid of formula

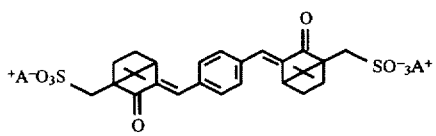

wherein

A represents hydrogen, alkali metal or $NH(R)_3^{30}$ wherein said R's each independently represent hydrogen, $C_1$–$C_4$ alkyl, $C_1$–$C_4$ hydroxyalkyl or $M^{n+}/n$ wherein $M^{n+}$ is a polyvalent metal cation wherein n represents 2, 3, or 4.

2. The screening cosmetic composition of claim 1 wherein $M^{n+}$ is a polyvalent metal cation selected from the group consisting of $Ca^{2+}$, $Zn^{2+}$, $Mg^{2+}$, $Ba^{2+}$, $Al^{3+}$ and $Zr^{4+}$.

3. The screening cosmetic composition of claim 1 comprising in a mixture, said titanium oxide nanopigment and an aluminum salt of said compound of formula (I).

4. The screening cosmetic composition of claim 1 wherein said titanium oxide nanopigment is present in an amount ranging from 1 to 7 percent by weight based on the total weight of said composition.

5. The screening cosmetic composition of claim 1 wherein said partially or completely neutralized 1,4 -benzenedi(3-methylidene-10-camphosulfonic) acid of formula (I) is present in an amount ranging from 0.25 to 5 percent by weight based on the weight of said acid relative to the total weight of said composition.

6. The screening cosmetic composition of claim 1 wherein said partially or completely neutralized 1,4-benzenedi(3-methylidene-10-camphosulfonic) acid/titanium oxide nanopigment weight ratio is between 0.05 and 5.

7. The screening cosmetic composition of claim 1 comprising a form selected from the group consisting of lotion, a thickened lotion, a gel, a vesicular dispersion, a cream, a milk, a powder, a solid stick, a foam and a spray.

8. The screening cosmetic composition of claim 7 which further contains a cosmetic adjuvant selected from the group consisting of a fatty substance; an organic solvent; a silicone; a thickener; a demulcent; a UV-A, UV-B or a broad-brand sunscreen agent; an antifoaming agent; a moisturizing agent; a perfume; a preservative; a surface-active agent; a filler; a sequesterant; an anionic, cationic, nonionic or amphoteric polymer or a mixture thereof; a propellant; an alkalizing agent; an acidifying agent; a colorant; and a metal oxide pigment having a particle size ranging from 100 nm to 20,000 nm.

9. The screening cosmetic composition of claim 1 for protecting human epidermis against ultraviolet rays or an anti-sun composition or for the prevention of photodermatoses, said composition being in a form selected from the group consisting of a suspension or dispersion in a solvent or fatty substance; an emulsion; a vesicular dispersion; an ointment; a gel; a solid stick; and an aerosol foam.

10. The screening cosmetic composition of claim 1 for protecting hair against ultraviolet rays, said composition being in a form selected from the group consisting of a rinse-off shampoo; a lotion; a gel (1) applicable before or after shampooing, (2) before or after dyeing or bleaching or (3) before, during or after permanent waving or hair straightening; a hair styling or treatment lotion or gel; a lotion or gel for blow-drying or hair setting; a hair lacquer; a permanent waving composition; a hair straightening composition; a hair dyeing composition and a hair bleaching composition.

11. The screening cosmetic composition of claim 1 comprising a make-up for eyelashes, eyebrows, skin or hair in a form selected from the group consisting of an epidermis treatment cream; a foundation; a lipstick; an eyeshadow; a blusher; an eyeliner; a mascara; and a coloring agent; said composition being provided in anhydrous or aqueous solid or paste form.

12. A process for protecting the human epidermis and hair against ultraviolet radiation comprising applying to the skin or hair a cosmetically effective amount of said screening cosmetic composition of claim 1.

13. A process for preventing the development of photodermatoses comprising applying to the skin a cosmetically effective amount of said screening cosmetic composition of claim 1.

14. A process for reducing or inhibiting light-induced reaction of titanium oxide nanopigments exposed to light comprising admixing in a cosmetically acceptable carrier 0.5 to 10% by weight of said titanium oxide nanopigments, having a mean diameter between 5 and 50 nm, with 0.1 to 10% by weight of partially or completely neutralized 1,4-benzenedi(3-methylidene-10 -camphosulfonic) acid of formula

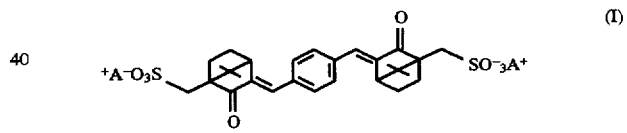

wherein

A represents hydrogen, alkali metal or $NH(R)_3^+$ wherein said R's each independently represent hydrogen, $C_1$–$C_4$ alkyl, $C_1$–$C_4$ hydroxyalkyl or $M^{n+}/n$ wherein $M^{n+}$ is a polyvalent metal cation wherein n represents 2, 3, or 4.

* * * * *